(12) United States Patent
Smith et al.

(10) Patent No.: US 7,781,214 B2
(45) Date of Patent: *Aug. 24, 2010

(54) LINEAGE SPECIFIC CELLS AND PROGENITOR CELLS

(75) Inventors: Austin G. Smith, Edinburgh (GB); Meng Li, Edinburgh (GB)

(73) Assignee: The University Court of the University of Edinburgh, Edinburgh (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/620,193

(22) Filed: Jan. 5, 2007

(65) Prior Publication Data

US 2007/0172946 A1      Jul. 26, 2007

Related U.S. Application Data

(60) Division of application No. 11/129,333, filed on May 16, 2005, which is a continuation of application No. 09/686,880, filed on Oct. 12, 2000, now Pat. No. 6,929,948, which is a continuation of application No. PCT/GB99/01136, filed on Apr. 14, 1999.

(30) Foreign Application Priority Data

Apr. 14, 1998  (GB) .................................. 98-7935.3

(51) Int. Cl.
  *C12N 15/00*  (2006.01)
  *C12N 5/08*  (2006.01)
  *C12N 15/63*  (2006.01)
  *A01N 63/00*  (2006.01)
  *C07H 21/04*  (2006.01)

(52) U.S. Cl. .................... 435/377; 435/320.1; 435/368; 435/455; 424/93.21; 536/24.1

(58) Field of Classification Search .............. 435/320.1, 435/368, 377, 455; 424/93.21; 536/24.1
  See application file for complete search history.

(56) References Cited

U.S. PATENT DOCUMENTS

| | | | |
|---|---|---|---|
| 5,602,301 A | 2/1997 | Field | |
| 5,629,145 A | 5/1997 | Meryman | |
| 5,654,183 A | 8/1997 | Anderson et al. | |
| 5,733,727 A | 3/1998 | Field | |
| 6,015,671 A | 1/2000 | Field | |
| 6,146,888 A * | 11/2000 | Smith et al. | 435/325 |
| 6,399,300 B1 | 6/2002 | Field | |
| 6,737,054 B2 | 5/2004 | Field | |
| 6,818,210 B2 | 11/2004 | Field | |
| 6,929,948 B1 * | 8/2005 | Smith et al. | 435/377 |

FOREIGN PATENT DOCUMENTS

| | | |
|---|---|---|
| WO | WO 93/18137 | 9/1993 |
| WO | WO 94/02593 | 2/1994 |
| WO | WO 94/24274 | 10/1994 |
| WO | WO 97/04118 | 2/1997 |
| WO | WO 99/10488 | 3/1999 |

OTHER PUBLICATIONS

Villeneuve et al., 1983, Molecular and Cellular Biology, vol. 3, No. 12, p. 2271-2279.*
Linzhao Cheng et al., "Sustained Gene Expression in Retrovirally Transduced, Engrafting Human Hematopoietic Stem Cells and Their Lympho-Myeloid Progeny," *Blood*, 92:83-92, 1998.
E. Conneally at al., "Rapid and Efficient Selection of Human Hematopoietic Cells Expressing Murine Heat-Stable Antigen as and indicator of Retroviral-Mediated Gene Transfer," *Blood*, 87:456-464, 1996.
Ericson et al., *Cell*, 90:169-180, 1997.
Gradwohl et al., *Dev. Biol.*, 180:227-241, 1996.
Meng Li at al., "Generation of purified neural precursors from embryonic stem cells by lineage selection," *Current Biology*, 8:971-974, 1998.
Stem Cells: A Primer, *Natl. Inst. Health*, 2000:1-6.
Xu et al., *J. Biol. Chem.*, 272;3430-3436, 1997.

* cited by examiner

*Primary Examiner*—Shin-Lin Chen
(74) *Attorney, Agent, or Firm*—Finnegan, Henderson, Farabow, Garrett & Dunner, LLP

(57) ABSTRACT

A method for generating a culture that is purified or enriched in respect of cells of a selected lineage is described in which a selectable marker, which is differentially expressed in cells of the selected lineage compared with its expression in other cells, is introduced into a multipotential cell and the multipotential cell is cultured to induce differentiation of the multipotential cell into a cell of the selected lineage or into a mixture of cells including cells of the selected lineage, or is cultured to induce preferential survival of cells of the selected lineage. Those cells that express the selectable marker are then selected for. Progenitors of selected lineage are also described as is the use of the method in assay techniques.

19 Claims, 14 Drawing Sheets

*FIG. 3* NEURAL STEM CELL (NSC) SELECTION STRATEGY
I. TARGETING MARKER INTO NEURAL PRECURSOR-SPECIFIC GENE IN ES CELLS
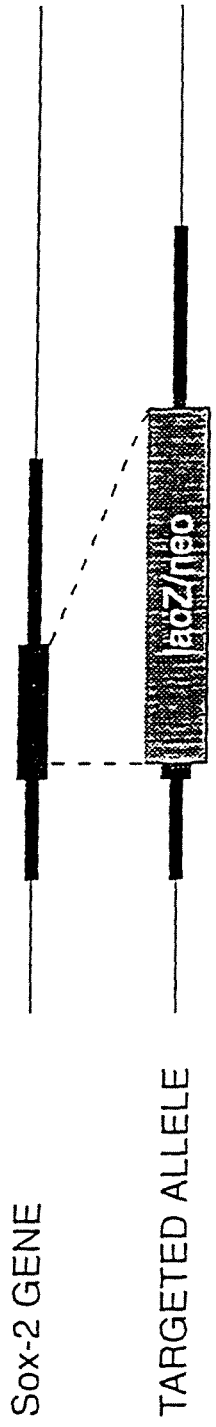
Sox-2 GENE
TARGETED ALLELE
II. ELIMINATION OF NON-NEURAL CELLS FROM DIFFERENTIATING ES CELL CULTURES
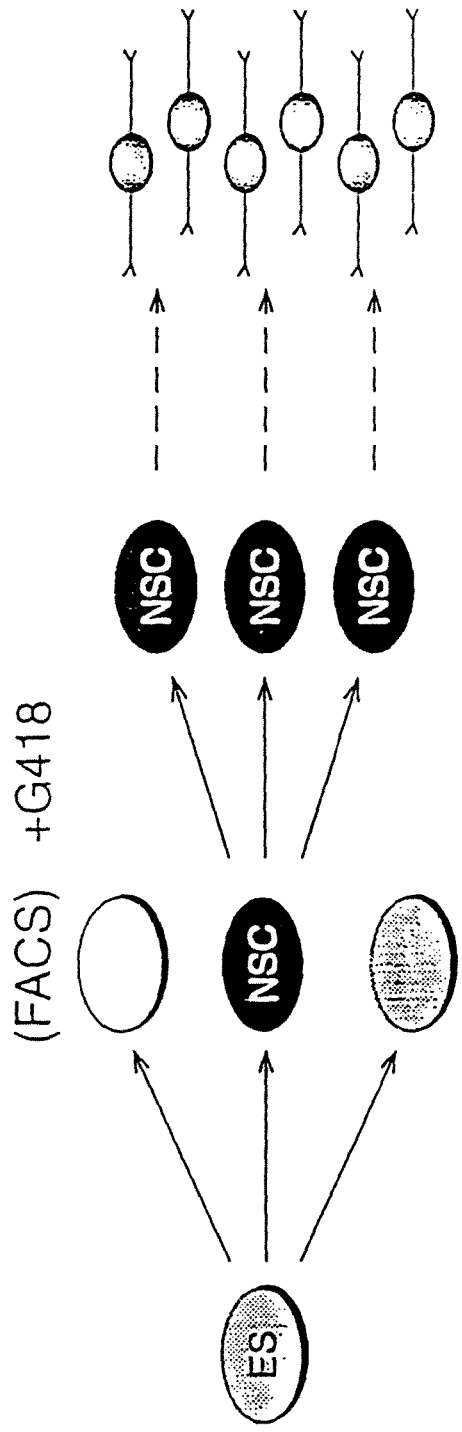

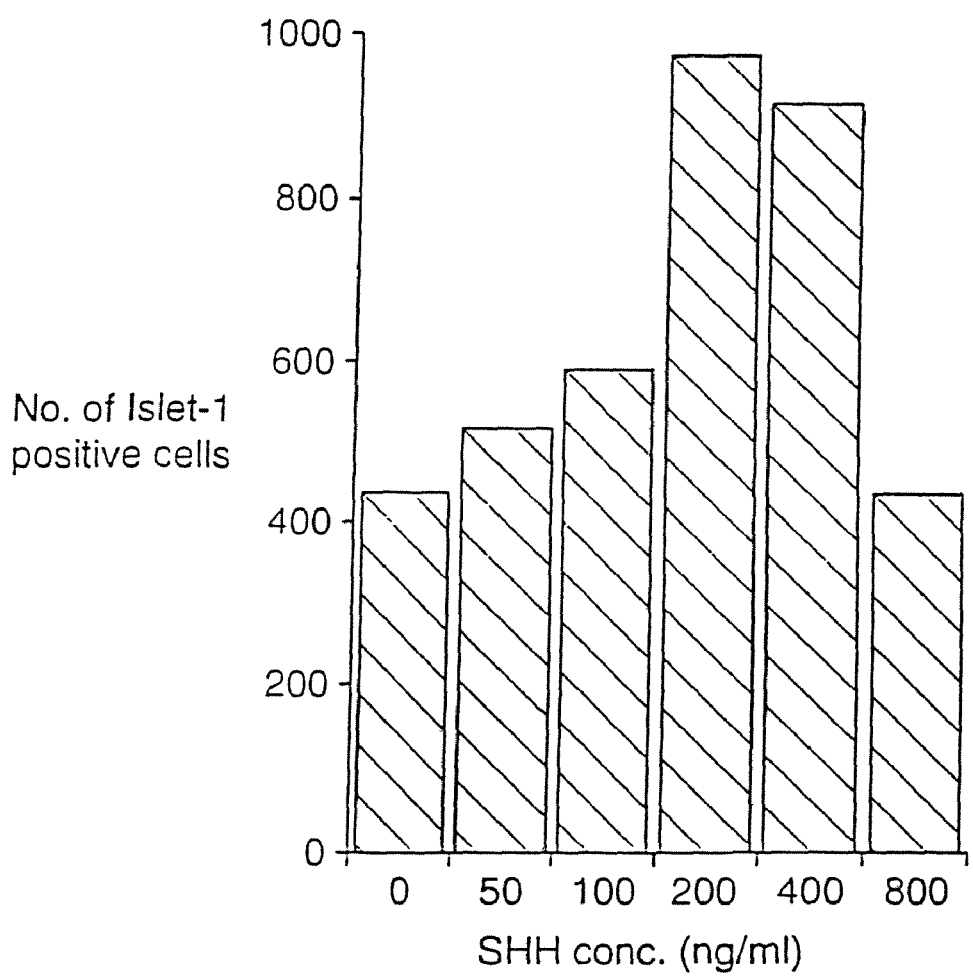
FIG. 8 INDUCTIVE EFFECT OF SONIC HEDGEHOG ON ES-DERIVED NEURAL PRECURSORS

LINEAGE SPECIFIC CELLS AND PROGENITOR CELLS

This is a divisional of application Ser. No. 11/129,333, filed May 16, 2005, which is a continuation of application Ser. No. 09/686,880, filed Oct. 12, 2000, now U.S. Pat. No. 6,929,948, which is a continuation of Serial No. PCT/GB99/01136, filed Apr. 14, 1999, all of which are incorporated herein by reference.

This invention relates to lineage specific cells and progenitor cells, methods of obtaining them and their uses. Pluripotent embryonic stem (ES) cells can be induced to differentiate in vitro into a mixture of cell types, comprising extraembryonic yolk sac and derivatives of all three embryonic germ layers. However, the disorganised and heterogeneous nature of the differentiation impedes manipulation and analysis of individual lineages. In particular, the invention provides a lineage-specific genetic selection technique to establish purified populations of neural precursors from differentiating ES cells.

Embryonic stem (ES) cells are non-transformed cell lines derived directly from the pluripotent founder tissue in the mouse or human embryo, the epiblast (Evans and Kaufman, 1981; Martin, 1981; Brook and Gardner, 1997; Thomson et al, 1998; Shamblott et al, 1998). ES cells can be propagated and extensively genetically manipulated whilst retaining the capacity for multilineage differentiation, both in vivo and in vitro (Robertson, 1987). The differentiation of ES cells in culture closely reflects differentiative events in the embryo. In principle, therefore, ES cells provide in vitro access to the instructive and selective processes by which cellular diversification is generated in the mammalian embryo (Smith, 1992).

Multilineage differentiation of ES cells can be initiated by simple aggregation (Martin and Evans, 1975; Doetschman et al., 1985). The aggregates form structures known as embryoid bodies, differentiation of which mirrors aspects of peri- and early post-implantation mouse embryogenesis (Martin et al., 1977; Doetschman et al., 1985). A diverse array of cell types are subsequently found in outgrowths from embryoid bodies (Weiss and Orkin, 1996). Although representation of particular lineages can be diminished or enhanced by treatment with dimethyl sulphoxide or retinoic acid (RA), the differentiated products always consist of a mixture of cell types. This intrinsic disorganisation and complexity have limited the exploitation of in vitro ES cell differentiation for assignment of gene functions in developmental pathways.

Several reports have documented the presence of neuronal cells and glia (Bain, 1995; Fraichard et al., 1995; Strubing et al., 1995; Okabe et al., 1996) in embryoid body outgrowths. This could be exploited to detect, characterise and manipulate factors that regulate neurogenesis and neuronal and glial differentiation. ES cells could also be used as a source of normal or genetically manipulated neural cells for biochemical and functional studies or for transplantation. The problem is that these objectives, however, are severely compromised by the abundance of non-neural cells in the cultures and because it is not currently possible to establish or maintain a culture predominantly containing neural cell progenitors.

The art thus fails to provide a reliable method of obtaining a substantially pure population of a cell of any selected lineage, and progenitor cells of a selected lineage in particular. The art also fails to provide assays for developmental and other effects of factors on progenitor cells or differentiated cells of a selected lineage.

The present invention aims to provide progenitor cells and/or differentiated cells of a selected lineage, assays for the effect of factors on such cells and uses of these cells, such as in transplantation. The present invention further aims to provide a genetic selection technique to eliminate non-neural cells from cultures and to enable purification from embryoid bodies of differentiation competent neural precursors.

The present invention provides a method of obtaining a culture of cells of a selected lineage having a combination of two steps. One step is to select for cells that express a gene characteristic of cells of that lineage. The other is to so culture cells that they tend to differentiate into or proliferate as cells of that lineage. The effect is to yield a more highly purified culture of the selected-lineage cells than is otherwise possible.

By way of example, one step of the combination is to select for cells that express a gene known to be expressed uniquely in haematopoietic progenitor cells, and the other is to culture cells in medium containing a nutrient known to promote differentiation of cells into haematopoietic progenitors.

Accordingly, the invention provides a method for generating a culture that is purified or enriched in respect of cells of a selected lineage, comprising:-
  (i) introducing into a multipotential cell a selectable marker that is differentially expressed in cells of the selected lineage compared with its expression in other cells;
  (ii) culturing the multipotential cell to induce (a) differentiation of the multipotential cell into a cell of the selected lineage or into a mixture of cells that is or includes cells of the selected lineage or (b) preferential survival of cells of the selected lineage; and
  (iii) selecting for those cells that express the selectable marker, The method is suitable for obtaining cells, optionally progenitors, of the selected lineage at high purity. Whilst following the art method for inducing differentiation of ES cells into a culture that includes neural cells can provide a maximum of about 50% neural progenitors, using the technique of the invention a purity in excess of 70% can be obtained, and in a specific embodiment described below the purity is substantially 100%.

Step (ii) results in a pure population of cells or a mixed culture at least slightly purified or enriched in respect of desired cells and can suitably be carried out by culturing the multipotential cell in the presence of a factor that induces differentiation of the cell into a progenitor cell of the selected lineage. By way of example, a mitogen specific for neural progenitors is fibroblast growth factor. Reference herein to the term "factor" is not intended to be limited to protein or polypeptide factors but is intended to encompass any biologically active molecule or potentially biologically active molecule.

The multipotential cell may be selected from embryonic stem (ES) cells, embryonic germ (EG) cells, embryonal carcinoma (EC) cells, a primary culture of foetal cells, a primary culture of post-natal cells and a primary culture of adult cells. The method may further comprise genetically modifying cells to delete, mutate, substitute or add genes in order to assay gene function in progenitor cells of the selected lineage or adapt a cell phenotype to render it more suitable for transplantation. The cells may thus be obtained by introducing a selectable marker into a multipotential cell line or a primary culture containing the cells of interest and then selecting out the cells of interest. The selectable marker is optionally introduced by transfection or viral infection via a transgenic animal from which the primary cultures are then established, suitably using the methods described in WO-A-94/24274.

The invention thus advantageously enables a highly enriched population of cells and in particular all lineages of progenitors of a chosen lineage to be obtained. In an example below the population obtained is substantially 100% pure making it possible to isolate a single cell of known progenitor lineage. The invention is of application to all lineages of cells particularly progenitor cells. A selectable marker expressed in cells that express a Sox gene leads to neural progenitor cells; the CD34, CD44 and SCL genes are suitable for obtaining haematopoietic progenitors, and the Nkx 2.5 or GATA-4 gene for cardiac progenitors. For generating myogenic progenitors, MyoO or myE5 are suitable. Using retinoic acid induces differentiation of ES cells into neural cells, DMSO induces differentiation into haematopoietic cells and absence of retinoic acid induces a population enriched in cardiac progenitors.

The method optionally further comprises:-
(iv) introducing into the multipotential cell a second selectable marker that is differentially expressed in progenitor cells or other cells of a selected sub-lineage compared with its expression in other cells, wherein cells of the selected sub-lineage are formed by differentiation of cells of the selected progenitor lineage; and
(v) when a culture of progenitor cells of the selected lineage has been obtained, allowing or inducing differentiation of the cells and selecting for cells that express the second selectable marker.

This aspect of the invention further enhances the purity of the obtained culture of cells, and is of advantage in cases that cells of the selected lineage differentially express a gene but only at a level slightly different from non-desired cells.

In a preferred embodiment of the invention, described in more detail below, the selectable marker is a gene that codes for antibiotic resistance and selecting for those cells that express the selectable marker comprises introducing antibiotic into the culture. In use, application of the antibiotic selectively kills or ablates cells that do not express the marker, leaving behind a population of cells purified or enriched in respect of those expressing the antibiotic resistance, i.e. viable cells of selected lineage. At least two ways of introducing the selectable marker are known and suitable for the invention. The selectable marker may be introduced into the multipotential cell by targeted integration or gene trapping into a gene that is differentially expressed in progenitor cells of the selected lineage. Expression of the selectable marker is thereby operatively linked to a gene differentially expressed in a desired pattern. The selectable marker may also be introduced into the multipotential cell via random integration as a transgene wherein it is expressed under control of the regulatory elements of a gene that is differentially expressed in progenitor cells of the selected lineage.

The selectable marker may more generally be a marker that when expressed results in preferential survival of cells expressing the marker, with antibiotic resistance being one such example. In this instance the marker is expressed in cells of the selected lineage. The selectable marker may also be a marker whose expression results in preferential killing of cells expressing the marker. In this instance the marker is expressed in cells other than those of the selected lineage.

In a specific embodiment of the invention described in an example below, the multipotential cell is an ES, EC or EG cell and the method comprises inducing differentiation of the multipotential cell—one way is to form an embryoid body from the cell—and dissociating the cells. Trypsin is used in one example. It is an advantage that individual cells are thereby obtained. These are all exposed to the culture medium and not being attached to neighbouring cells are free of cell-to-cell influences that might affect the pattern of growth and/or differentiation of the cells, and hinder formation of progenitor cells according to the invention.

A culture that is purified or enriched in respect of ventral progenitor cells is obtainable according to the invention, wherein the selectable marker is differentially expressed in neural progenitor cells and the second selectable marker is differentially expressed in ventral progenitor cells. The second selectable marker for this is suitably differentially expressed in cells that express Pax 6.

A culture that is purified on enriched in respect of dorsal progenitor cells is obtainable according to the invention, wherein the selectable marker is differentially expressed in the neural progenitor cells and the second selectable marker is differentially expressed in dorsal progenitor cells. The second selectable marker for this is suitably differentially expressed in cells that express Pax 3.

The invention also provides a cell, preferably a progenitor, of a selected lineage, obtainable according to the method of the invention. Hitherto, preparations of progenitors were too impure for certainty as to whether any chosen cell was a progenitor cell. With culture according to the invention that can give rise to substantially 100% pure preparations of progenitors, isolation of a single progenitor is achieved.

The invention further provides a composition comprising a plurality of cells, wherein a majority of the cells are progenitor cells of a selected linage. Preferably, at least 60% of the cells are progenitor cells of the selected lineage. More preferably, at least 60% of the cells are neural progenitor cells. In addition, the invention provides an isolated neural progenitor cell.

A significant application of the invention is in the field of assaying factors for the effects they may have on a selected progenitor. Accordingly, the invention still further provides an assay of the effect of a factor on a culture of progenitor cells of a selected lineage, comprising:-
(i) introducing into a multipotential cell a selectable marker that is differentially expressed in cells of the selected lineage compared with its expression in other cells;
(ii) culturing the multipotential cell to induce differentiation of the multipotential cell into a cell or mixture of cells that includes cells of the selected lineage or to induce preferential survival of cells of the selected lineage;
(iii) selecting for those cells that express the selectable marker; and
(iv) culturing the thereby obtained cells of selected lineage in the presence of the factor.

The assay method is preferably for assay of the effect of a factor on a culture of progenitor cells of selected lineage, wherein the selectable marker is differentially expressed in those progenitor cells. Reference to a "factor" in the assay, is intended to be a reference to any actual or potential biologically active molecule that may be introduced into culture of cells of the selected lineage, and is thus not intended to be limited to protein and polypeptide factors. The term is also intended to encompass a gene introduced or modified in a multipotential cell from which cells of the selected lineage are obtained. The assay can thus conveniently be used to assay for the effect of a particular gene, as well as for the effect of polypeptide and/or protein factors or small molecules of interest.

The method can be used to assay whether the factor has a proliferative, maturation, toxic or protective effect on progenitor cells of the selected lineage, or whether a factor has a proliferative, maturation, cytotoxic or glial protective effect on neural progenitor cells or on other differentiated cells obtained following withdrawal of selection and differentiation of the progenitors.

It is an advantage of the assay method that it enables a population of terminally differentiated cells of selected lineage to be obtained and used for such assays as gene and drug discovery screens.

Yet further provided by the invention is a neural progenitor cell, or a culture comprising a majority of neural progenitor cells, for transplantation. In an example below, a neural progenitor cell of the invention has been successfully isolated and transplanted into the brain of a rat. The neural cell may optionally be a neuronal cell or a glial cell.

This transplantation can also be carried out using neuronal cells obtained from neural progenitors of the invention. A suitable method of generating purified neurons comprises obtaining a culture purified in respect of neural progenitors, using the method of the invention wherein the selectable marker is differentially expressed in cells that express a Sox gene, and culturing the progenitors obtained in the presence of medium suitable for differentiation of the progenitors into neurons. A suitable method of generating a purified glial cells comprises obtaining a culture purified in respect of neural progenitors, using the method of the invention wherein the selectable marker is differentially expressed in cells that express a Sox gene, and culturing the progenitors obtained in the presences of medium suitable for differentiation of the progenitors into glial cells.

Yet further the invention provides a neural progenitor cell for transplantation to treat neurodegenerative disease or neuronal/brain injury, a neural progenitor cells for transplantation, obtainable from a cell selected from an ES cell, an EC cell, an EG cell a primary culture of foetal cells and a primary culture of post-natal cells, for transplantation to treat neurodegenerative diseases or neuronal/brain injuries, a method of treatment of neurodegenerative disease or neuronal/brain injury comprising transplantation of a neural progenitor cell, and a method of preparing a neural progenitor cell or a differentiated progeny thereof for storage, comprising obtaining the cell in a method according to the invention and freezing the cell in the presence of a cryoprotectant, such as 10% dimethyl sulfoxide.

In an embodiment of the invention, a selection/reporter gene, βgeo, was integrated by homologous recombination into the sox2 gene, which is expressed uniformly in precursor cells in the neural plate and neural tube. Application of G418 to differentiating cultures of sox2-targeted cells resulted in the efficient isolation of viable βgeo-positive cells. These cells expressed markers of neuroepithelial precursor cells. They differentiated efficiently into networks of neuron-like cells that expressed a variety of neuronal markers. Thus, an in vitro system for genetic and molecular dissection of mammalian neural differentiation is provided by the invention, and also a route for the production of pure populations of normal or genetically modified neural precursors and neurons for functional studies including transplantation. Furthermore, the lineage selection approach of the invention is applicable to the isolation of other precursor populations from differentiating ES cell cultures.

The invention still further provides a method of amplifying a purified population of progenitor cells of a selected lineage, comprising
maintaining the cells in culture in the presence of
a mitogen; and
a growth factor.

The progenitor cells preferably comprise a gene coding for a selectable marker, which gene is differentially expressed in the progenitor cells compared with its expression in other cells, and the method further comprises selecting for cells that express the selectable marker. It is an option to maintain the culture over a plurality of generations and periodically select for cells that express the selectable marker.

Another option is to maintain the culture over a plurality of generations and continuously select for cells that express the selectable marker. Where the selectable marker is antibiotic resistance the method may thus comprise continuous culture in the presence of antibiotic.

The invention is now described with reference to the accompanying drawings in which:-

FIG. 3 shows a schematic diagram of lineage selection according to the invention;

FIG. 8 shows results of assay of effect of sonic hedgehog on neural progenitors.

Figure 1A:
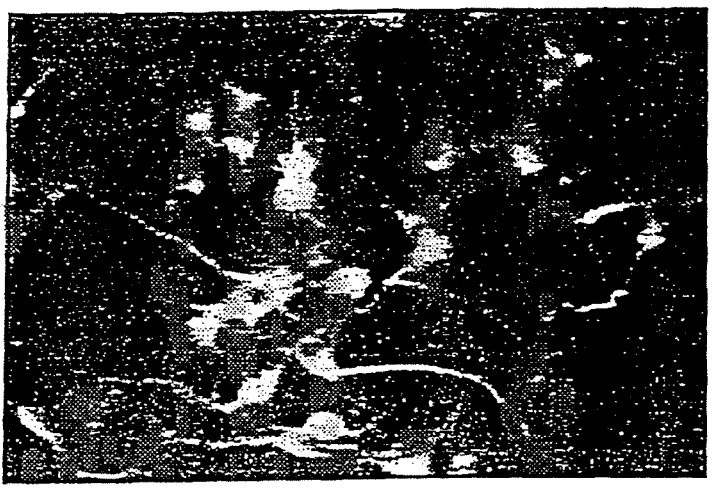
FIG. 1 shows morphology and characterization of neurons and glia in day 4 cultures.
Figure 1B:
Figure 1C:
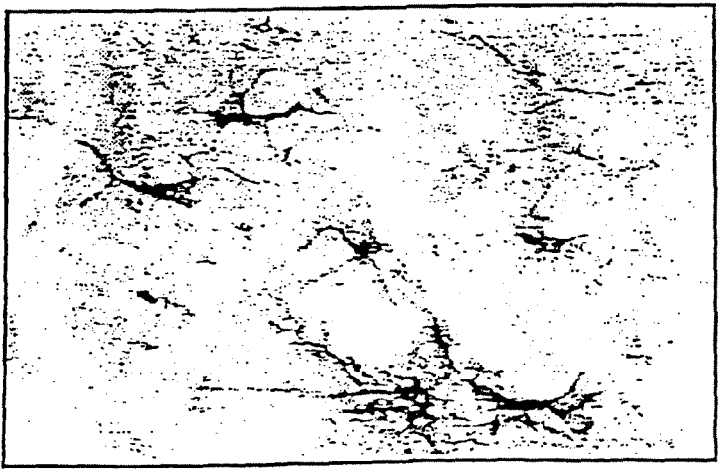

In more detail, FIG. 1 shows morphology and characterization of neurons and glia in day 4 cultures. E14TG2a ES cells were induced to differentiate in aggregates for 8 days, plated on poly-D-lysine/laminin substrate in DMEM/F12 supplemented with N2. Cells were photographed alive with phase-contrast optics after 4 days in culture. The majority of the cells are neuronal-like, their neuritic processes connected into a cellular network. (a), (b) and (c) show cultures that were stained with anti-NFL, anti-MAP2, and anti-GFAP, respectively.

In FIG. 4, ES cells with a targeted insertion of, βgeo into the Sox2 gene were induced to differentiate by culture as aggregates ("embryoid bodies"). After 4 days they were exposed to $10^{-6}$ M retinoic acid for a further 4 days. The aggregates were then dissociated and cells plated on poly-D-lysine and laminin-coated dishes in serum-free medium with N2 supplement. Cultures were unselected or exposed to G418 either for the final 48 hours of aggregate culture (b, f, h, i) or for 24 hours after plating (d):
a. Sox2-linked β-galactosidase expression in unselected culture 3 hours after plating.
b. Sox2-linked β-galactosidase expression in G418-selected culture 3 hours after plating.
c. Sox2-linked β-galactosidase expression in unselected culture 24 hours after plating.
d. Sox2-linked β-galactosidase expression in G418-selected culture 24 hours after plating.
e. Immunostaining with anti-Sox2 of unselected culture 3 hours after plating.
f. Immunostaining with anti-Sox2 of G418-selected culture 3 hours after plating.
g. DAPI counterstaining of panel e.
h. DAPI counterstaining of panel f.
i. Double-labelling with anti-nestin (green) and anti-Sox2 (red/orange) of G418-selected culture 3 hours after plating.

The scale bar indicates 100 μm for (a,b,c,d), 66.7 μm for (e,f, g, h) and 50 μm for (i).

For FIG. 5, Sox2 expressing cells were selected with G418 for 2 days in EB cultures, cells were dissociated and allowed to attach to culture dishes for 3 hours before fixation. The expression for Pax3 (a), delta-1 (b), Mash-1 (c) and Math-4a (d) were detected by in situ hybridisation with specific antisense riboprobes; the presence of Pax6-expressing cells were detected by staining the culture with an anti-Pax6 antibody (e), culture e was double labelled with DAPI to localize nuclei of all cells (f). Scale bar, 100 μm.

Figure 6A:
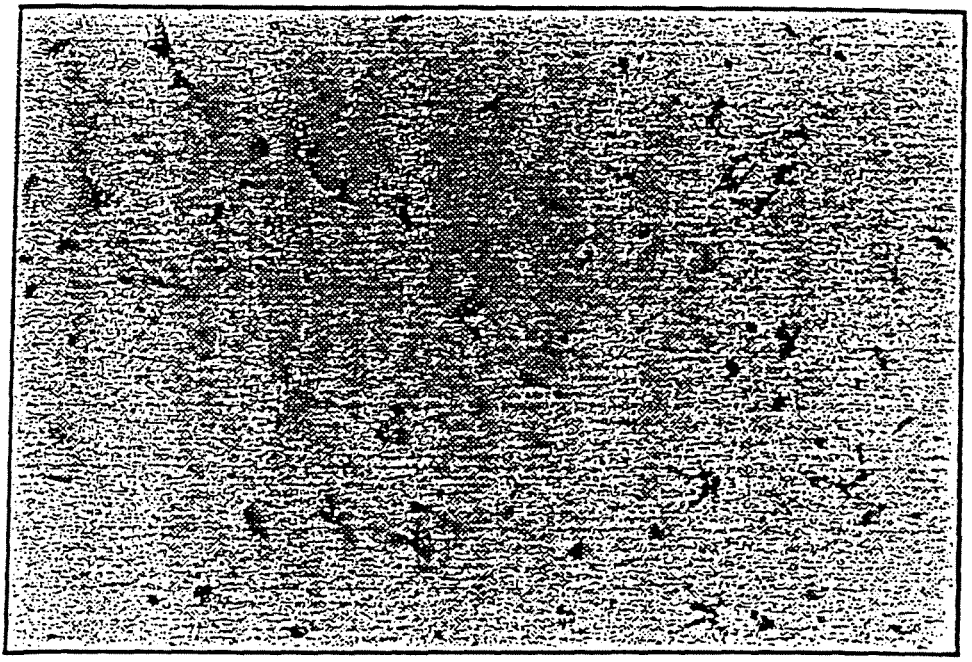
FIG. 6 shows Sox2 positive cells proliferate in vitro in response to FGF-2.
Figure 6B:
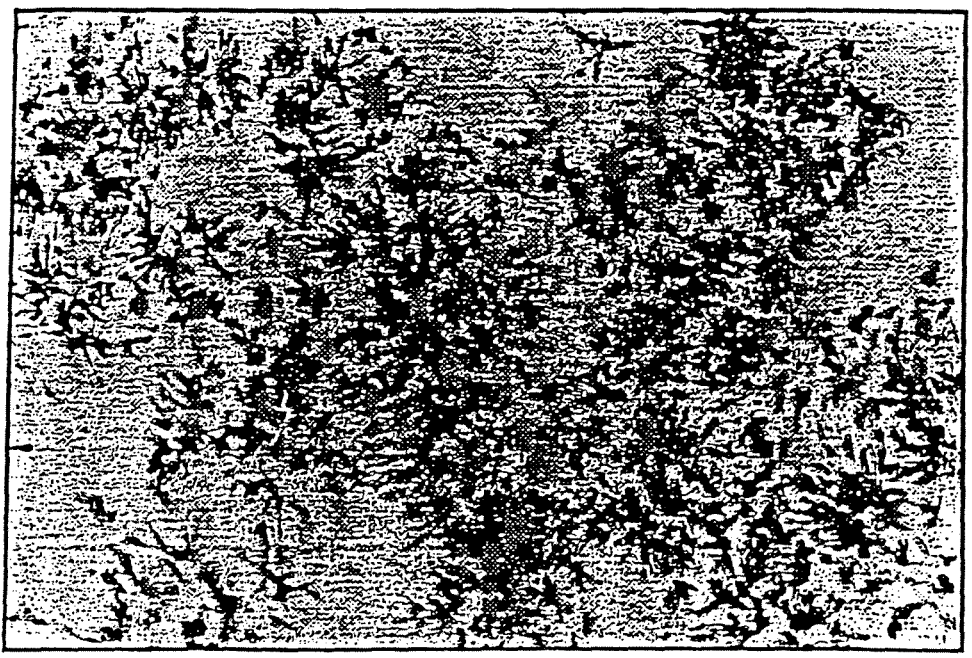

For FIG. 6, following 8 days induction of neural differentiation, cells were dissociated by trypsinization, plated at low density, and cultured in DMEM/F12 supplemented with N2 medium in the presence of 10 ng/ml of bFGF and 200 μg/ml of G418. (a) overnight culture; (b), 4 day culture. Cell numbers increased around 10 fold over the culture period. Cells expanded in the presence of bFGF maintained Sox2 expression as shown via X-gal staining. Scale bar: 50 μm.

For FIG. 7, Sox2-expressing cells selected by 48 hours exposure to G418 during embryoid body culture were plated and grown in the absence of G418 in N2 medium for 48 hours (a and b) or 96 hours (c-e), or for 72 hours followed by a further 72 hours in Neurobasal medium plus B27 supplement and 2% horse serum (f-i) (Scale bar, 100 μm):

a,b. Double immunolabelling showing down-regulation of Sox-2 (a) in newly differentiating cells expressing the neuronal marker β-tubulin 3 (b).
c. Immunostaining for neuronal marker, β3-tubulin with propidium iodide counterstaining showing neuronal differentiation of >90% of cells.
d,e. Double immunolabelling for neuronal markers synapsin-I (d) and MAP2/Tau (e).
f. Immunostaining for GABA
g. Phase contrast image of field in f.
h. Immunostaining for glutamate.
i. Phase contrast image of field in h.

In FIG. 8, CCE-sox2 ES embryoid bodies undergoing g418 selection were exposed to the indicated concentrations of recombinant sonic hedgehog protein. Cells were fixed and immunostained for the motorneuron marker islet 1/2 48 hours after dissociation.

Figure 9:
FIG. 9 shows an ES cell-derived neuron after transplantation in utero.

In FIG. 9, sox-2 expressing cells selected by exposure to g418 during embryoid body culture were dissociated, labelled with PKH26-GL (Sigma) and injected into the forebrain vesicles of E16 rat foetuses in utero. Pregnancy was then allowed to go to term. Pups were sacrificed on P2. Vibratome sections were prepared and examined by fluorescence microscopy. The figure shows a representative PKH26-GL labelled cell within the cortex exhibiting typical immature neuronal morphology. This study demonstrates that Sox2 selected cells can integrate and differentiate in the brain.

Materials and Methods

ES Cell Culture

ES cell lines used in this study were: E14TG2a (Hooper et al., 1987), CGR8 (Mountford et al., 1994) and CCE-Sox2, a derivative of CCE (Bradley et al., 1984) in which one copy of the Sox2 gene has been disrupted by homologous recombination. All ES cell lines were maintained in gelatin-coated tissue culture plastic in Glasgow modified Eagle's medium (GMEM) supplemented with $10^{-4}$ 2-mercaptoethanol, 10% fetal calf serum (FCS) and 100 U/ml LIF (Smith, 1991).

Induction of Differentiation.

The basic protocol is based on that described (Bain, 1995). ES cells were lightly trypsinized into small clumps and allowed to aggregate in suspension culture in the absence of LIF. After 4 days culture, all trans-retinoic acid (RA) was added at a concentration of $10^{-6}$M. After a further 4 days aggregates were dissociated by incubation with trypsin and trituration. Cells were seeded at $3\times10^5$ cells/well into 4-well dishes (Nunc) coated with poly-D-lysine and laminin. Culture medium was serum-free DMEM/F12 (50/50) supplemented with N2 and, where specified, B27 (Gibco-BRL) plus 2% horse serum.

Substrate Preparation.

Tissue culture plates were precoated with poly-D-lysine (PDL, 30-70 kDa, Sigma) for 20 min at a concentration of 10 μg/ml in PBS. Excess PDL was withdrawn and the plates were rinsed with PBS three times before coating with laminin (Sigma) at a concentration of 2-10 ?g/ml in PBS overnight at 4° C.

Immunocytochemistry

Staining for Sox1 and Sox2 was carried out on cultures fixed in MEMFA (4% formaldehyde, 100 mM MOPS pH 7.4, 20 mM EGTA, 1 mM MgSO$_4$) for 1 hour. To stain cells with antibodies against GABA and glutamate, cells were fixed with 1% glutaraldehyde in PBS (Turner, Neurochemistry). For detection of other intracellular antigens, cultures were fixed in 4% paraformaldehyde in PBS for 15 min. Fixed cells were rinsed with PBS, incubated with blocking buffer (PBS, 1 mg/ml BSA, 0.1% Triton X-100, and 1% goat serum) for 30 min followed by incubation with primary antibodies in blocking buffer overnight at 4° C. Cells were then rinsed with PBS, and incubated with a species specific secondary antibody in blocking buffer for 1 hr. Cultures were washed with three changes of PBS, mounted with Vectashield mounting media (Vector) and examined under a fluorescent microscope.

Double labelling experiments were performed by simultaneously incubating cells in appropriate combinations of primary antibodies, followed by incubation with non-cross-reactive secondary antibodies. In some experiments, cultures were counter stained with propidium iodide or DAPI at concentrations of 1 ng/ml and 5 μg/ml respectively.

The following dilutions were used for primary and secondary antibodies: rabbit anti-Sox1 and anti-Sox2 (1:500), rabbit anti-GABA (1:2000, Sigma), rabbit anti-glutamate (1:4000, Sigma), mouse anti-β-tubulin 3 (1:200, Sigma); mouse anti-NF68 (1:400, Sigma); rabbit anti-MAPs, which reacts with MAP2 and Tau (1:400, Sigma); mouse anti-GFAP (1:400, Sigma), mouse anti-synapsin-I (1:50, Chemicon), mouse anti-nestin (1:50, DSHB), mouse anti-Pax6 (1:10, - - - ). Cy3-conjugated goat anti-mouse IgG (1/50, Jackson ImmunoResearch), FITC-conjugated goat anti-mouse IgG (1:100, Sigma), FITC-conjugated goat anti-rabbit Ig (1:100, Sigma), TRITC-conjugated goat anti-rabbit Ig (1:50, Sigma).

In situ Hybridization of Cultured Cells.

The protocol is based on that of (Rosen and Beddington, 1993) adapted for cultured cells. Briefly, cultures were fixed in 4% paraformaldehyde and permeabilized at -20° C. in 100% methanol. The cells were then rehydrated through a series of methanol and finally put into PBS with 0.1% Tween-20. Prehybridization was performed for 1-4 hr in hybridization buffer (50% ultrapure formamide, 5×SSC, pH 4.5, 50 mg/ml heparin, 100 μg/ml herring sperm DNA and tRNA, 0.1% Tween-20), the digoxigenin (DIG)-labeled probes were added at 1 μg/ml overnight at 70° C. Washes the following day were three times for 30 min at 65° C. in wash buffer (50% formamide, 2×SSC, 0.1% Tween-20), three 5 min washes in TBST (137 mM NaCl, 25 mM Tris-HCl, pH 7.6, 3 mM KCl, 0.1% Tween-20) and 1 hr block in 10% serum/TBST. Cells were then incubated overnight at 4° C. with alkaline phosphatase-coupled anti-DIG antibody (1:2000, Boehringer-Mannheim). The following day cells were washed three times 1 hr with TBST and three times for 10 min with alkaline phosphatase buffer (APB, 100 mM NaCl, 100 mM Tris pH 9.5, 50 mM $MgCl_2$, 0.1% Tween-20). The alkaline phosphatase staining reaction was allowed to proceed for 3 hr to overnight with 4.5 µl/ml NBT an 3.5 µl/ml BCIP in APB (Boehringer).

DIG-labeled RNA Probes

The murine cDNAs used as templates for riboprobes were a 519 bp Pax3 fragment (provided by Dr Rosa Beddington), a 700 bp Delta-1 clone (provided by Dr Domingos Henrique), a 670 bp Mash-1 fragment and a 1.5 kb Math-4A cDNA (both were provided by Dr Francois Guillemot). DNAs were linearized and RNA synthesis was directed using T7, T3 or SP6 RNA polymerase, including DIG-labeled nucleotide mix as recommended by the suppliers (Boehringer). Products were analyzed on a 0.8% agarose gel and approximately 1 µg/ml of the DIG-labeled antisense RNA was used for hybridization of cells.

Detection of β-galactosidase

Cells were fixed in fix buffer (0.2% glutaraldehyde, 0.1 M phosphate buffer pH 7.2, 2 mM MgCl2, 5 mM EGTA) for 10 min at 4° C. and washed three times with wash buffer (0.1 M phosphate buffer pH 7.2, 2 mM $MgCl_2$). The cells were then incubated at 37° C. overnight with 1 mg/ml 5-bromo-4-chloro-3-indolyl-µ-D-galactoside (X-gal), 4 mM potassium fericyanide, 4 mM potassium ferrocyanide in wash buffer (Beddington et al., 1989).

Results

Efficient Generation of Neurons and Glia from ES Cells

Induction of neural differentiation was based on published methods (Bain, 1995; Fraichard et al., 1995) in which ES cells are aggregated in suspension to form embryoid bodies, exposed to retinoic acid, and then allowed to reattach and outgrow on a substrate. Under these conditions neuronal like cells become evident in the outgrowths after several days accompanied by a variety of other cell types. We introduced two variations into the protocol which enhanced the final representation of neuronal cells. First, the embryoid bodies were dissociated before plating. This results in a homogeneous dispersion and immediately terminates inductive and selective effects within the embryoid bodies. Second, cells were plated in a defined neuronal culture medium (DMEM/F12 plus N2) on substrates coated with poly-D-lysine and laminin which support attachment and outgrowth of neuronal cells. Each of these procedures had an additive effect on the proportion of neural cells in the cultures. When combined, more than 50% of viable cells 4 days after plating had extended processes and where immunoreactive for neuronal markers neurofilament light and heavy chains, MAP2/tau, or, tubulin III (FIG. 1 and data not shown). A smaller proportion of cells, around 20%, expressed the astrocyte marker GFAP (not shown). Significantly this observation is not cell line specific as comparable results were obtained with three independent ES cell lines and several subclones.

Non-neural cell types remained in these cultures, however, often identifiable as large, flat non-refractile cells. If, at any point, DMEM/F12 plus N2 was supplemented with serum or mitogens (FGF-2 or B27 supplement), these non-neural cells expanded rapidly and progressively became the predominant cell type.

Detection of Sox1/Sox2 Expressing Neural Progenitors

Figure 2A:
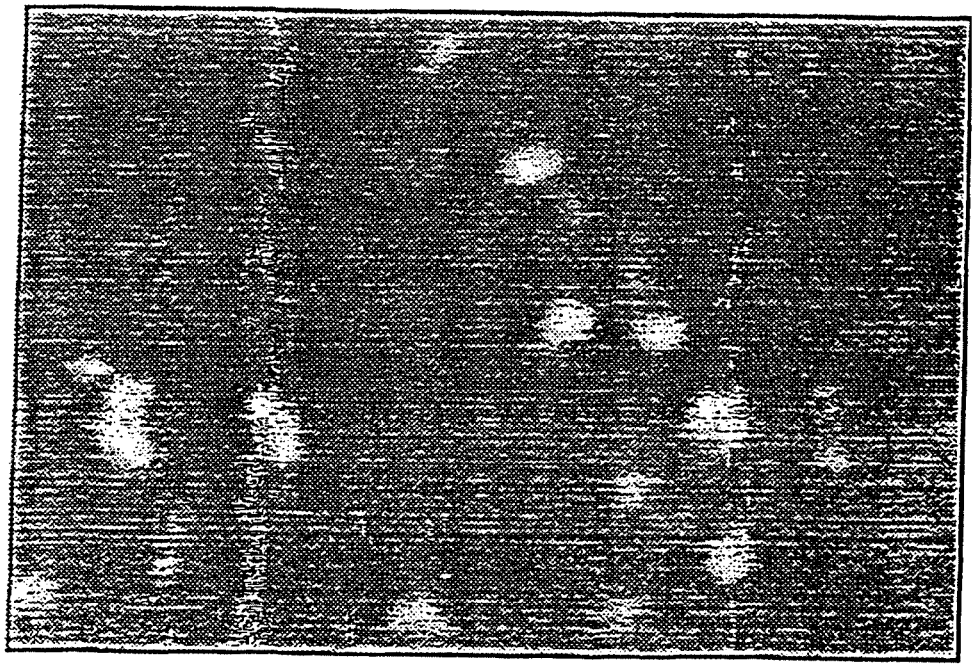
FIG. 2 shows phase contrast picture of day 0 cells (2a—4 hours following plating), and Sox1 antibody staining (2b)—scale bar is 50 microns.

The generation of a large proportion of differentiated neurons and glia suggested that neural precursor cells might be detectable at an earlier time point in the differentiation protocol. FIG. 2a shows a representative culture 4 hours following plating. At this stage, cells appear to be morphologically undifferentiated. The soma of the majority of cells are small, elongated or oval shaped. Some cells have short processes similar in length to their cell bodies. These morphological features are similar to primary neural precursors reported previously (Kalyani et al., 1997). These cells do not express detectable NF-L or GFAP 3 hours after plating. After overnight culture, less than 1% of the population were positive for either of these two markers.

Figure 2B:
Figure 4A:
FIG. 4 shows culture enrichment for Sox2-positive cells by G418 selection.
Figure 4B:
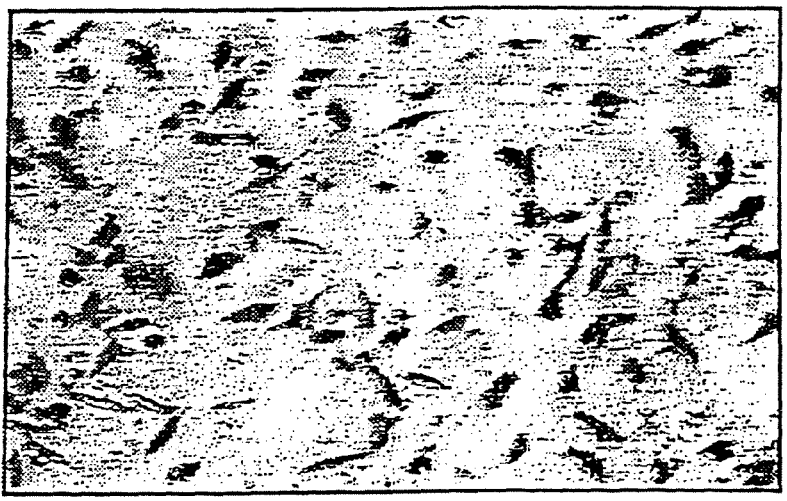
Figure 4C:
Figure 4D:
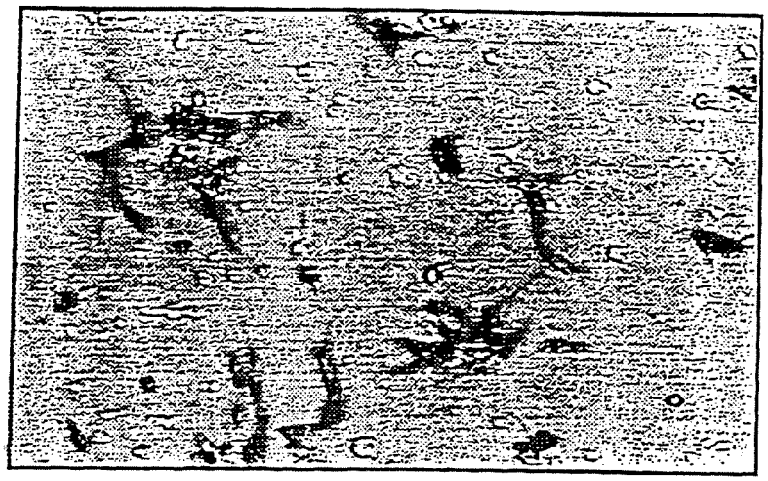
Figure 4E:
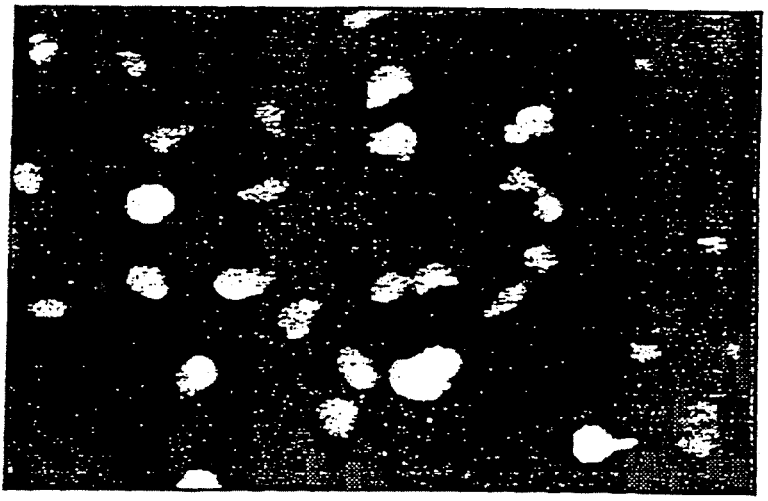
Figure 4F:
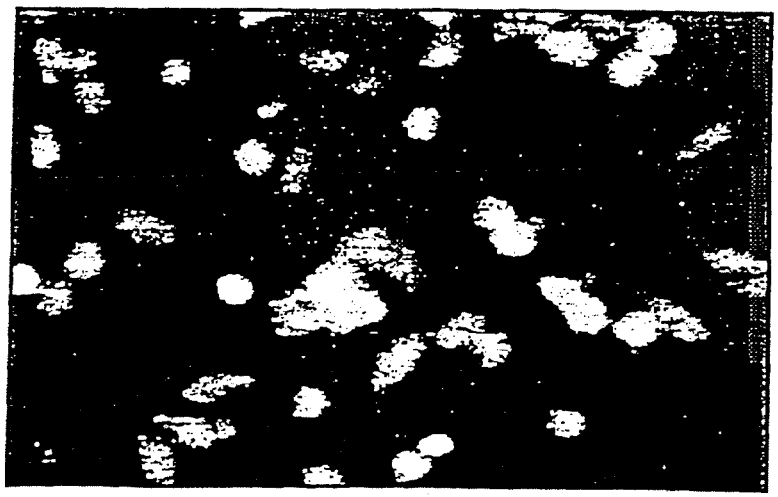
Figure 4G:
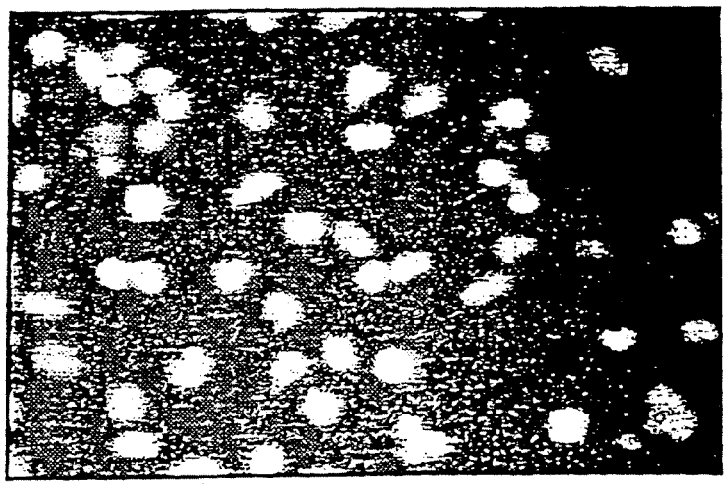
Figure 4H:
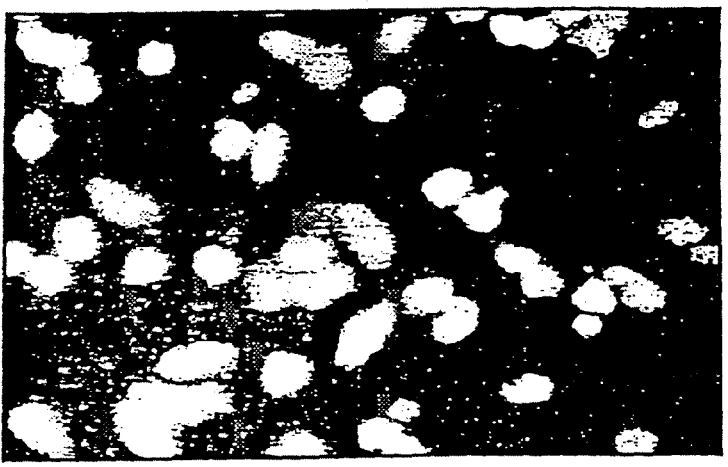
Figure 4I:
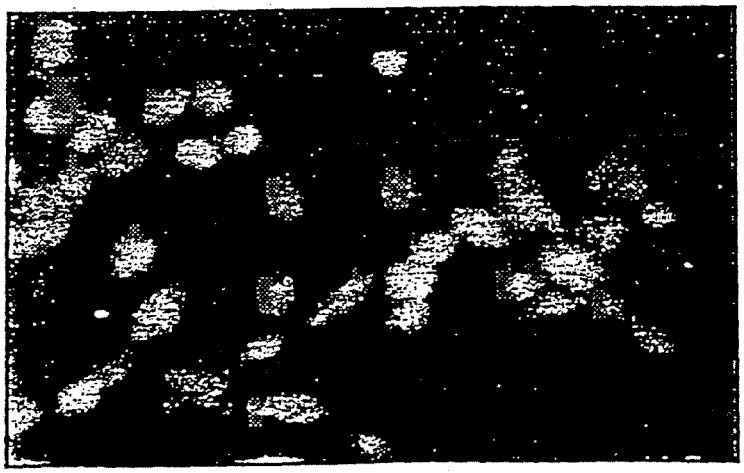
Figure 5A:
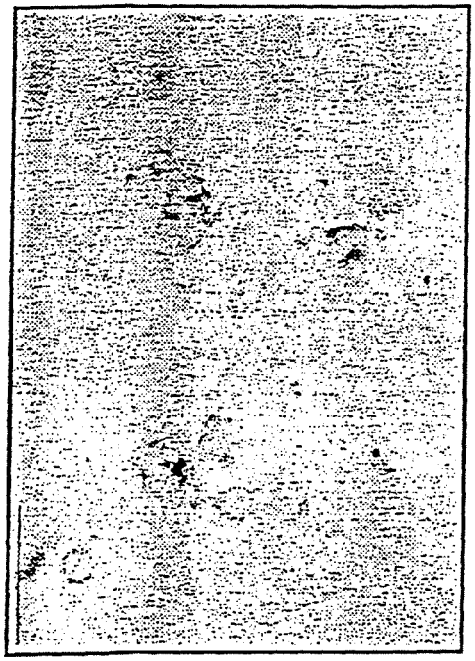
FIG. 5 shows expression of region-specific neural precursor markers.
Figure 5B:
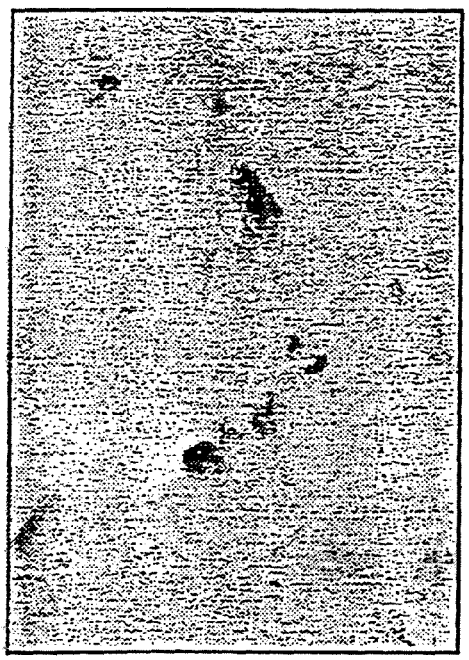
Figure 5C:
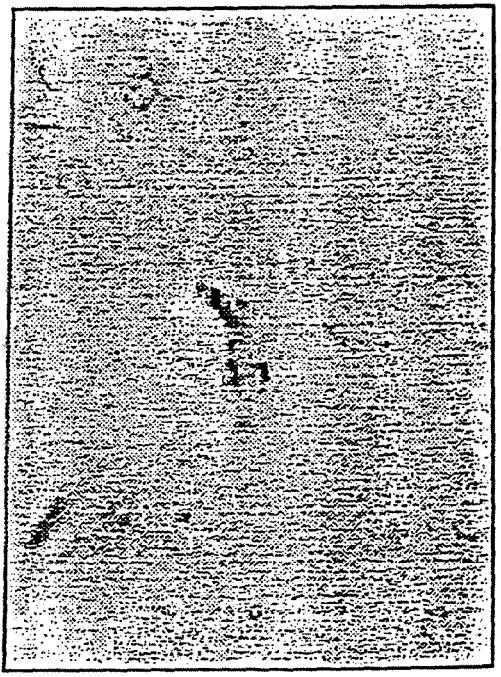
Figure 5D:
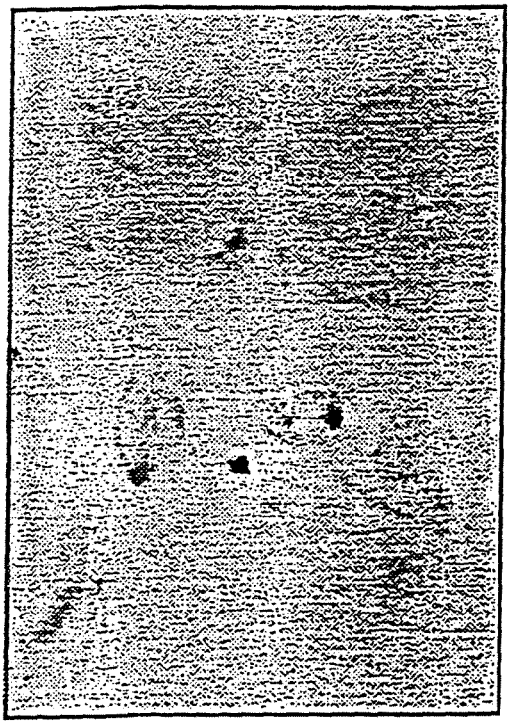
Figure 5E:
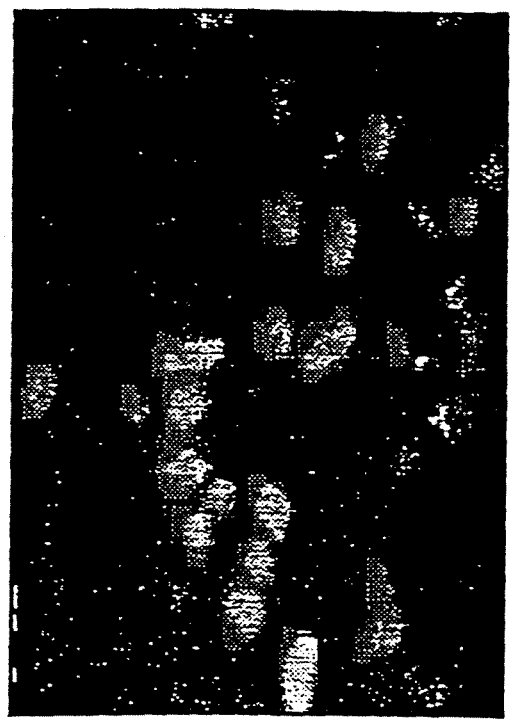
Figure 5F:

The cultures were examined for presence of the intermediate filament, nestin (Lendahl et al., 1990), which is expressed in neuroepithelial cells. Almost all cells were nestin-positive, however, presumably because the expression of nestin is not strictly restricted to neuroepithelium [Hockfield, 1985 #868]. We therefore sought a more specific marker. The SRY-related transcription factor Sox1 is confined to the neuroepithelium of the neural plate and dividing neural progenitors in the early mouse embryo (Pevny, unpublished data). The related Sox2 gene is expressed in an overlapping pattern that also encompasses floor plate and early neural crest cells. Immunostaining of freshly plated cells with antibodies raised against Sox1 and Sox2 revealed that 40-50% of the cells were positive (FIG. 2b and FIG. 3e). These cells likely correspond to neural progenitors.

Selection and Purification of Sox2-expressing Neural Progenitor Cells.

To isolate the neural progenitor pool we used ES cells in which the bifunctional selection marker/reporter gene, βgeo has been integrated into the Sox2 gene by homologous recombination (ref). When induced to differentiate as described above, approximately 50% of these cells stained for, β-galactosidase activity (FIG. 2 and Table 1), consistent with the proportion of cells that express Sox2 protein. We applied G418 to the differentiating cultures to eliminate Sox2-negative non-neural cells (FIG. 3).

G418 (200 µg/ml) was added after retinoic acid induction, either during embryoid body culture or upon plating. In both conditions appreciable cell killing was evident. Crucially, however, large numbers of cells survived that exhibited typical neuroepithelial morphology. Over 90% of these cells gave prominent β-galactosidase staining (FIG. 4). Concordance with Sox2 protein expression was confirmed by immunostaining (FIG. 4, Table 1). The related HMG-box factor Sox1, an exclusive marker of pluripotential neural plate stage cells and of CNS-restricted precursors in the neural tube, was detectable in the great majority of cells. Almost all viable cells expressed nestin.

Sox2-selected Cells Express Markers of Neural Progenitor Specification.

The developmental organisation and subdivision of the central nervous system is underpinned by the temporal and spatial patterning of gene expression (Tanabe and Jessell, 1996). In order to gauge the diversity of neural differentiation that could be achievable from ES cells in the absence of embryonic axial organisation, we have begun to examine expression of key determinants, Pax genes and neurogenic bHLH transcription factors.

The paired box transcription factors Pax3 and Pax6 are found in dividing neural precursors throughout the length of the embryonic neural tube. Pax3 is initially expressed in the neural plate and subsequently becomes confined to the dorsal half of the neural tube (Liem et al., 1995). Pax6 is expressed predominantly in the ventral region of the neural tube (Walther and Gruss, 1991; Tanabe and Jessell, 1996). Widespread expression of both pax genes was found in sox-2 selected cells analysed on the day of plating (FIG. 5 and Table 2). This suggests that ES cell-derived neural precursors can acquire both dorsal and ventral identities.

The bHLH genes, mash1 and math4A (neurogenin) show a more restricted localisation to subsets of neural progenitors. Expression of each was readily detected in sox2-selected cultures, but in significantly fewer cells than the pax gene products (FIG. 5, Table 2). It is likely that the expression of mash1 and math4A specifies distinct sub-populations of progenitors, as the distribution of these two transcription factors is mutually exclusive in most CNS regions (Gradwohl et al., 1996).

Two early markers of neuronal differentiation were also examined. The notch ligand delta1, which is found in committed cells immediately prior to neuronal differentiation (ref), was expressed in only 1-2% of cells immediately after plating, indicating that the majority of the cells are not yet committed to terminal differentiation (see also Discussion). Expression of the LIM homeodomain protein islet-1/2, an early marker of differentiation of motor neurons and ventral interneurons (Ericson et al., 1992), was examined in Sox2-selected cultures 48 hours after plating. Reproducibly 1-2% of cells were immunoreactive at this stage (not shown).

Sox2-selected Cells Proliferate in Response to FGF-2.

Several studies have presented evidence that basic fibroblast growth factor (FGF-2) can support proliferation of primary neural progenitors and immortalised progenitor cell lines (Palmer et al., 1997). Addition of FGF-2 (10 ng/ml) to Sox-2 selected cultures likewise stimulated cell proliferation. FIG. 6 shows a typical Xgal-stained culture following addition of FGF-2. It can be seen that all cells retain relatively undifferentiated morphology and show strong Xgal staining. Such cultures could be expanded and serially passaged for at least two weeks.

Neuronal Differentiation of Sox2-selected Cells.

Figure 7A:
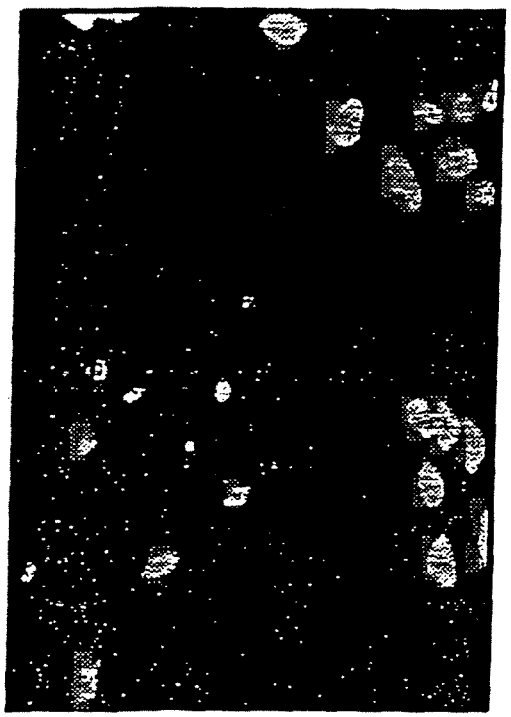
FIG. 7 shows ES cell-derived neurons differentiated following Sox2-selection.
Figure 7B:
Figure 7C:
Figure 7D:
Figure 7E:
Figure 7F:
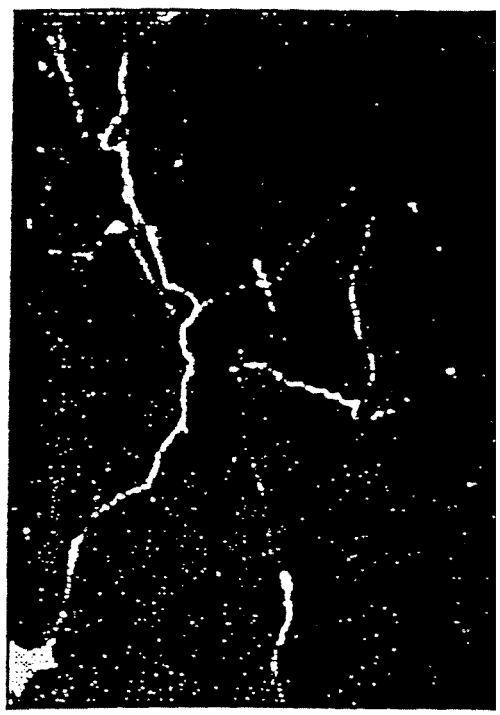
Figure 7G:
Figure 7H:
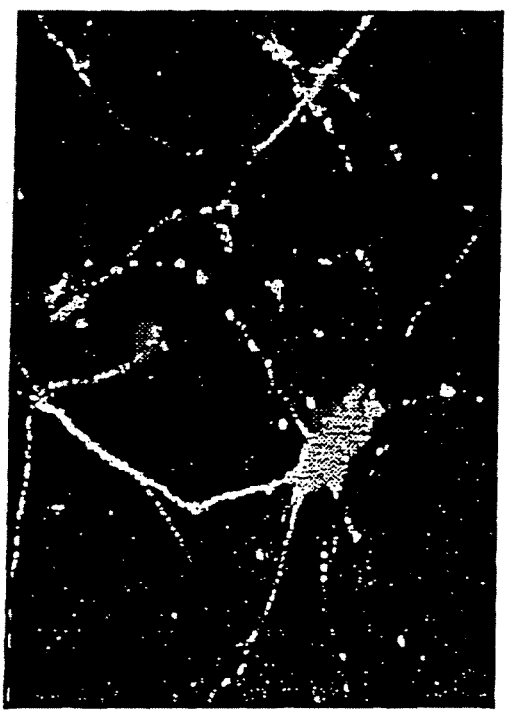
Figure 7I:
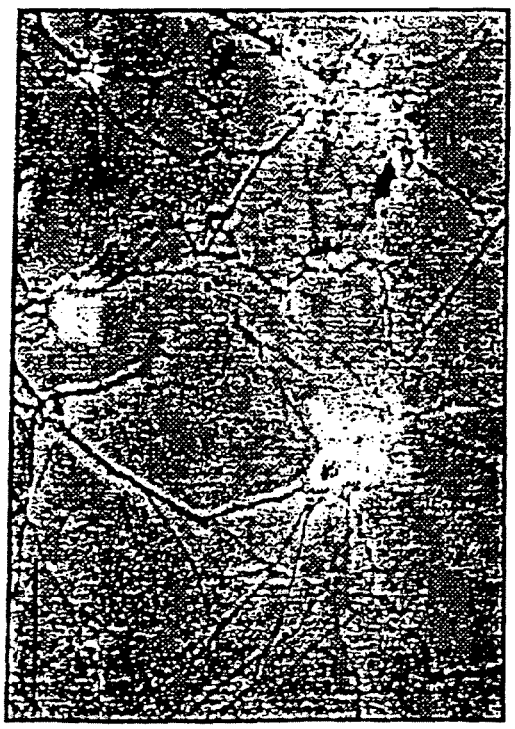

In order to determine whether the Sox2-selected precursor cells retained the capacity for neuronal differentiation, G418 was removed from the medium. Within 48 hours the cells began to extend neuritic processes and by 96 hours a network of neuron-like cells had formed (FIG. 7). β-galactosidase activity was lost from the majority of cells (not shown) consistent with the down-regulation of Sox2 in differentiating neurons (ref). Immunostaining confirmed the disappearance of Sox2 protein (FIG. 7b). Pan-neuronal markers neurofilament light and heavy chain (not shown), microtubule associated proteins (MAPs/tau), β-tubulin III (Lee et al., 1990) and synapsin I were detectable from 48 hours onwards, co-incident with down-regulation of Sox2. By 96 hours over 90% of cells had long dendritic processes and expressed neuronal markers (FIG. 7). Supplementation of the culture medium with B27 and horse serum allowed further maturation of the neuronal cells, evidenced both by increased sprouting of dendrites and by production of excitatory and inhibitory neurotransmitters GABA and glutamate (FIG. 7)

The mammalian nervous system is derived from neuroepithelial cells of the neural tube and its derivative neural crest. During neurogenesis, these neural progenitors proliferate, progressively lose their multipotentiality and finally differentiate into various type of post mitotic neurons and glial cells [Anderson, 1993 #673, McKay, 1989 #672(Tanabe and Jessell, 1996; McKay, 1997)]. The mechanisms involved in the determination and differentiation of neural precursor cells are the subject of intense investigation. This has been hitherto hindered, however by the relative inaccessibility and tissue complexity of the mammalian embryo. An in vitro model system of the present invention in which neuroepithelial cells can be derived and undergo proliferation and differentiation provides a powerful tool to study intrinsic and extrinsic factors that determine neural specification and differentiation.

ES cells have the capacity to develop into any cell type as evidenced by their colonisation of all lineages in chimaeras (Beddington and Robertson, 1989). The prospect of using ES cells to dissect developmental pathways in vitro has been frustrated, however, by an inability to control or direct differentiation. In an embodiment of the invention described above, there is provided a strategy for selecting precursors of the lineage of interest from developing embryoid bodies. Our results demonstrate that viable neural precursors can be isolated by selection for Sox2 gene activity. These cells can be induced to proliferate or to differentiate into neurons. Therefore the survival and development of the neural lineage in vitro does not require continued interaction with other cell types. Moreover, the finding that significant cellular components can be ablated without causing disintegration of the embryoid bodies, nor apparently perturbing development of the surviving cells is both surprising and encouraging for the application of this approach to other lineages. Indeed it is possible that such ablation may favour the maintenance and expansion of specific stem cell populations by removing sources of differentiation inducing signals, which may be either cells from other lineages or more mature cells of the same lineage (Mountford and Smith, in personal communication).

The heterogenous expression of determination genes (FIG. 5) within the Sox2 selected cultures appears reflective of the subspecification of progenitors within the neural tube. Requirements for induction, growth and differentiation of individual progenitor types could therefore be investigated, both by addition of extracellular regulators to the culture system and by genetic manipulation of the ES cells prior to differentiation. The latter particularly relevant to situations where homozygous gene deletion ortransgene expression in vivo cause embryonic lethality. In addition, the ability to produce genetically modified neurons is likely to find significant applications in neuronal cell biology and biochemistry.

It has recently been reported that differentiated ES cells injected into the developing (Brustle et al., 1997) or even adult (Deacon et al., 1998) rodent brain can colonise the host nervous system and give rise to mature neuronal phenotypes. Such transplants also contain non-neuronal cells, however. These foreign cells can give rise to teratomas and other benign or malignant growths. They may also interfere with trophic signalling and guidance cues from host tissue to injected neural cells. Prior isolation of the neural precursors according to the invention eliminates these problems. Furthermore, following application of lineage selection purified neural cells can be accessed at any stage of in vitro maturation and harvested for transplantation.

The invention opens the way for development of human multipotential stem cells analogous to the mouse ES cells of an example above for clinical use in transplantation. Neurodegenerative conditions such as Parkinson's and Huntington's diseases are potentially treatable by cell replacement strategies and present compelling cases for development of a renewable stem cell resource for production of transplantable cells (Svendsen and Rosser, 1995; Rosenthal, 1998). The lineage selection approach, in combination with appropriate instructive factors, is a valuable component of such a system, by enabling the generation of a defined cell population from a multipotent source.

REFERENCES

Bain, G., Kitchens, D., Yao, M., Huettner, J. E., Gottlieb, D. I. 1995. Embryonic stem cells express neuronal properties in vitro. Dev. Biol. 168: 342-357.

Beddington, R. S. P., J. Morgenstern, H. Land, and A. Hogan. 1989. An in situ transgenic enzyme marker for the midgestation mouse embryo and the visualization of inner cell mass clones during early embryogenesis. Development 106: 37-46.

Beddington, R. S. P., and E. J. Robertson. 1989. An assessment of the developmental potential of embryonic stem cells in the midgestation mouse embryo. Development 105: 733-737.

Bradley, A., M. J. Evans, M. H. Kaufman, and E. Robertson. 1984. Formation of germ-line chimaeras from embryo-derived teratocarcinoma cell lines. Nature 309: 255-256.

Brook, F. A., and R. L. Gardner. 1997. The origin and efficient derivation of embryonic stem cells in the mouse. Proc. Natl. Acad. Sci. USA 94: 5709-5712.

Brustle, O., A. C. Spiro, K. Karram, K. Choudhary, S. Okabe, and R. G. D. McKay. 1997. In vitro-generated neural precursors participate in mammalian brain development. Proc. Nati. Acad. Sci. USA 94: 14809-14814.

Deacon, T., J. Dinsmore, L. C. Costantini, J. Ratliff, and O. Isacson. 1998. Blastula-stage stem cells can differentiate into dopaminergic and serotonergic neurons after transplantation. Exp. Neurol. 149: 28-41.

Doetschman, T. C., H. Eistetter, M. Katz, W. Schmidt, and R. Kemler. 1985. The in vitro development of blastocyst-derived embryonic stem cell lines: formation of visceral yolk sac, blood islands and myocardium. J. Embryol. Exp. Morphol. 87: 27-45.

Ericson, J., S. Thor, T. Edlund, T. M. Jessell, and T. Yamada. 1992. Early stages of motor neuron differentiation revealed by expression of homeobox gene Islet-1. Science 256: 1550-1560.

Evans, M. J., and M. Kaufman. 1981. Establishment in culture of pluripotential cells from mouse embryos. Nature 292: 154-156.

Fraichard, A., O. Chassande, G. Bilbaut, C. Dehay, P. Savatier, and J. Samarut. 1995. In vitro differentiation of embryonic stem cells into glial cells and functional neurons. J. Cell Sci. 108: 3181-3188.

Gradwohl, G., C. Fode, and F. Guillemot. 1996. Restricted expression of a novel murine atonal-related bHLH protein in undifferentiated neural precursors. Dev. Biol. 180: 227-241.

Hooper, M. L., K. Hardy, A. Handyside, S. Hunter, and M. Monk. 1987. HPRT-deficient (Lesch-Nyhan) mouse embryos derived from germline colonization by cultured cells. Nature 326: 292-295.

Kalyani, A., K. Hobson, and M. S. Rao. 1997. Neuroepithelial stem cells from the embryonic spinal cord: isolation, characterization and clonal analysis. Dev Biol 186: 202-223.

Lee, M. K., J. B. Tuttle, L. I. Rebhun, D. N. Cleveland, and A. Frankfurter. 1990. The expression and post-translational modification of a neuron-specific. ?-tubulin isoformduring chick embryogenesis. Cell. Motil. Cytoskeleton 17: 118-132.

Lendahl, U., L. B. Zimmerman, and R. D. G. McKay. 1990. CNS stem cells express a new class of intermediate filament protein. Cell 60.

Liem, K. F., G. Tremmi, H. Roelink, and T. M. Jessell. 1995. Dorsal differentiation of neural plate cells by BMP-mediated signals from epidermal ectoderm. Cell 82: 969-979.

Martin, G. R. 1981. Isolation of a pluripotent cell line from early mouse embryos cultured in medium conditioned by teratocarcinoma stem cells. Proc. Natl. Acad. Sci. USA 78: 7634-7638.

Martin, G. R., and M. J. Evans. (1975). The formation of embryoid bodies in vitro by homogeneous embryonal carcinoma cell cultures derived from isolated single cells. In "Teratomas and Differentiation" (M. I. Sherman and D. Solter, Eds.), pp. 169-187. Academic Press, New York.

Martin, G. R., L. M. Wiley, and I. Damjanov. 1977. The development of cystic embryoid bodies in vitro from clonal teratocarcinoma stem cells. Dev. Biol. 61: 230-244.

McKay, R. 1997. Stem cells in the central nervous system. Science 276: 66-71.

Mountford, P., B. Zevnik, A. Duwel, J. Nichols, M. Li, C. Dani, M. Robertson, I. Chambers, and A. Smith. 1994. Dicistronic targeting constructs: reporters and modifiers of mammalian gene expression. Proc. Natl. Acad. Sci. USA. 91: 4303-4307.

Okabe, S., K. Forsberg-Nilsson, A. C. Spiro, M. Segal, and R. D. G. McKay. 1996. Development of neuronal precursor cells and functional postmitotic neurons from embryonic stem cells in vitro. Mech. Dev. 59: 89-102.

Palmer, T. D., J. Takahashi, and F. H. Gage. 1997. The adult hippocampus contains primordial stem cells. Mol. Cell. Neurosci. 8: 389-404.

Robertson, E. J. (1987). "Teratocarcinoma and embryo-derived stem cells: a practical approach." IRL Press, Oxford.

Rosen, B., and R. S. P. Beddington. 1993. Whole-mount in situ hybridization in the mouse embryo: gene expression in three dimensions. Trends Genet. 9: 162-167.

Rosenthal, A. 1998. Auto transplants for Parkinson's disease? Neuron 20: 169-172.

Smith, A. G. 1991. Culture and differentiation of embryonic stem cells. J. Tiss. Cult. Meth. 13: 89-94.

Smith, A. G. 1992. Mouse embryo stem cells: their identification, propagation and manipulation. Semin. Cell Biol. 3: 385-399.

Strubing, C., G. Ahnert-Hilger, J. Shan, B. Wiedemann, J. Hescheler, and A. M. Wobus. 1995. Differentiation of pluripotent embryonic stem cells into the neuronal lineage in vitro gives rise to mature inhibitory and excitatory neurons. Mech. Dev. 53:275-287.

Svendsen, C. N., and A. E. Rosser. 1995. Neurones from stem cells. Trends Neurosci. 18: 465-467.

Tanabe, Y., and T. M. Jessell. 1996. Diversity and pattern in the developing spinal cord. Science 274: 1115-1123.

Thomson, J. A. et al. 1998. Embryonic Stem Cell. Lines Derived From Human Blastocysts. Science 282: 11145-7.

Shamblott, M. J. et al. 1998. Derivation Of Pluripotent Stem Cells From Cultured Human Primordial Germ Cells. Proc Natl Acad Sci 95(23): 13726-31.

Walther, C., and P. Gruss. 1991. Pax-6, a murine paired box gene, is expressed in the developing CNS. Development 113: 1435-1449.

Weiss, M. J., and S. H. Orkin. 1996. In vitro differentiation of murine embryonic stem cells. J. Clin. Invest. 97: 591-595.

TABLE 1

Expression of neuroepithelial markers following G418 selection

| Markers | −G418 | +G418 |
|---|---|---|
| | % positive staining (mean +/− SEM) | |
| β-galactosidase | 43.8 ± 9.4 | 91 ± 2.6 |
| Sox2 | 48.4 ± 1.1 | 95.5 ± 1.1 |
| Sox1 | 46.6 ± 5.6 | 88.7 ± 5.1 |
| Nestin* | 90 ± 6.5 | 94 ± 3.2 |

G418 was applied to EB cultures from the 6th day of induction at a concentration of 200 µg/ml. Two days later aggregates were trypsinized and the cell suspension was plated on poly-D-lysine/laminin coated substrate in DMEM/F12 plus N2. Cultures were fixed 3 hours after plating followed by histochemical staining for β-galactosidase with X-gal or immunocytochemical staining for Sox1, Sox2 and nestin with specific antibodies. Positively stained cells were scored under a 40× objective, seven to ten fields were counted for each sample. The result is given as an average percentage from two independent experiments (*Nestin is expressed in somitic mesoderm in addition to neuroepithelium).

The invention claimed is:

1. A method for generating a culture that is purified or enriched in neural progenitor cells, comprising:

(i) introducing into a pluripotent cell a selectable marker that is differentially expressed in neural progenitor cells compared with its expression in other cells, wherein neural progenitor cells constitute a sub-set of the cells obtainable from the pluripotent cell, and wherein expression of the selectable marker is under the control of a promoter of a gene that is differentially expressed in neural progenitor cells;

(ii) culturing the pluripotent cell in vitro in the presence of a factor that induces differentiation of the pluripotent cell to induce differentiation of the pluripotent cell into a neural progenitor cell or into a mixture of cells including neural progenitor cells, or to induce preferential survival, in a mixed culture of cells, of neural progenitor cells; and (iii) selecting for neural progenitor cells and against pluripotent cells according to differential expression of the selectable marker introduced in step (i), the selectable marker conferring preferential survival on the neural progenitor cells relative to the pluripotent cell of step (i);

thereby achieving directed differentiation of the pluripotent cell into a purified or enriched culture of neural progenitor cells.

2. A method for generating a culture that is purified or enriched in neural progenitor cells, comprising:

(i) obtaining a pluripotent cell which comprises a nucleotide sequence encoding a selectable marker under the control of a promoter of a gene that is differentially expressed in neural progenitor cells compared with its expression in other cells, wherein neural progenitor cells constitute a sub-set of the cells obtainable from the pluripotent cell;

(ii) culturing the pluripotent cell in vitro in the presence of a factor that induces differentiation of the pluripotent cell so as to induce differentiation of the pluripotent cell into a neural progenitor cell or into a mixture of cells including neural progenitor cells, or to induce preferential survival, in a mixed culture of cells, of neural progenitor cells;

(iii) selecting for neural progenitor cells and against the pluripotent cell of step (i) according to differential expression of the selectable marker, the selectable marker conferring preferential survival on the neural progenitor cells relative to the pluripotent cell of step (i); and (iv) propagating the neural progenitor cells obtained in (iii);

thereby achieving directed differentiation of the pluripotent cell into a purified or enriched culture of neural progenitor cells.

3. The method of claim 2, wherein the factor is retinoic acid.

4. The method of claim 2 wherein the pluripotent cell is selected from the group consisting of embryonic stem (ES) cells, embryonic germ (EG) cells, embryonic carcinoma (EC) cells.

5. The method of claim 2, further comprising genetically modifying pluripotent cells by deleting, mutating, substituting, or adding genes in said pluripotent cells in order to assay gene function in neural progenitor cells, or to render selected cells more suitable for transplantation, or both.

6. The method of claim 2, further comprising:

(v) introducing into the pluripotent cell a second selectable marker that is differentially expressed in cells of a selected sub-lineage compared with its expression in other cells, wherein cells of the selected sub-lineage are formed by differentiation of neural progenitor cells; and (vi) when a culture of neural progenitor cells has been obtained, allowing or inducing differentiation of the cells and selecting for cells that express the second selectable marker.

7. The method of claim 6, wherein the selectable marker is differentially expressed in neural progenitor cells and the second selectable marker is differentially expressed in ventral progenitor cells, thereby generating a culture that is purified or enriched in ventral progenitor cells.

8. The method of claim 7, wherein the second selectable marker is differentially expressed in cells that express Pax 6.

9. The method of claim 2, wherein the selectable marker is introduced into the pluripotent cell by targeted integration or random gene trap integration so as to be operatively coupled to a gene that is differentially expressed in neural progenitor cells.

10. The method of claim 2, wherein the selectable marker is introduced into the pluripotent cell via random integration of a transgene in which the selectable marker is operatively coupled to a gene that is differentially expressed in neural progenitor cells.

11. The method of claim 2, wherein the pluripotent cell is an ES, EG, or EC cell and the method comprises forming an embryoid body in step (ii), or otherwise inducing differentiation of the cells.

12. The method of claim 11, wherein the differentiated cells are dissociated so as to form a culture substantially of individual cells.

13. The method of claim 11, wherein differentiated cells of an embryoid body are dissociated using a protease.

14. The method of claim 2, wherein the selectable marker is an antibiotic resistance gene and the method comprises culture in the presence of antibiotic.

15. The method of claim 2, wherein expression of the selectable marker is operatively linked to expression of a gene selected from the group consisting of Pax 3, delta-1, Mash-1, and Math 4a.

16. The method of claim 2, further comprising freezing the cell in the presence of a cryoprotectant.

17. The method of claim 2, further comprising inducing differentiation of the propagated neural progenitor cells of (iii) into neurons.

18. The method of claim 17, wherein the propagated neural progenitor cells are induced to differentiate into neurons by culture in the presence of medium suitable for differentiation of the neural progenitor cells into neurons.

19. The method of claim 2, further comprising inducing differentiation of the propagated neural progenitor cells of (iii) into glia.

* * * * *

UNITED STATES PATENT AND TRADEMARK OFFICE
CERTIFICATE OF CORRECTION

PATENT NO. : 7,781,214 B2  Page 1 of 1
APPLICATION NO. : 11/620193
DATED : August 24, 2010
INVENTOR(S) : Austin G. Smith et al.

It is certified that error appears in the above-identified patent and that said Letters Patent is hereby corrected as shown below:

On the Title Page, Item (60), in the "Related U.S. Application Data", lines 3-4, delete the break between "6,929," and "948," (should read --6,929,948,--).

In claim 1, column 15, line 30, "in vitro" should read --*in vitro*--.

In claim 2, column 15, line 55, "in vitro" should read --*in vitro*--.

In claim 4, column 16, line 9, "claim 2 wherein" should read --claim 2, wherein--.

In claim 4, column 16, line 11, after "embryonic germ (EG) cells,", insert --and--.

Signed and Sealed this

Twenty-third Day of November, 2010

David J. Kappos
*Director of the United States Patent and Trademark Office*